(12) United States Patent
Hilfinger et al.

(10) Patent No.: US 7,176,185 B2
(45) Date of Patent: Feb. 13, 2007

(54) SHORT PEPTIDE CARRIER SYSTEM FOR CELLULAR DELIVERY OF AGENT

(75) Inventors: John Hilfinger, Ann Arbor, MI (US); Phillip Kish, Ann Arbor, MI (US)

(73) Assignee: TSRL, Inc., Ann Arbor, MI (US)

( * ) Notice: Subject to any disclaimer, the term of this patent is extended or adjusted under 35 U.S.C. 154(b) by 47 days.

(21) Appl. No.: 10/997,036

(22) Filed: Nov. 24, 2004

(65) Prior Publication Data

US 2005/0208140 A1 Sep. 22, 2005

Related U.S. Application Data

(60) Provisional application No. 60/524,836, filed on Nov. 25, 2003.

(51) Int. Cl.
*C07K 5/06* (2006.01)
(52) U.S. Cl. .................. 514/19; 530/331; 530/332; 530/345
(58) Field of Classification Search ............. 514/19; 530/331, 332, 345
See application file for complete search history.

(56) References Cited

U.S. PATENT DOCUMENTS

| | | | |
|---|---|---|---|
| 4,465,668 A | 8/1984 | Nishikido et al. | 424/177 |
| 4,559,325 A | 12/1985 | Burzynski | 514/21 |
| 4,603,012 A | 7/1986 | Zanno et al. | 530/998.21 |
| 5,364,650 A * | 11/1994 | Guthery | 510/111 |
| 5,854,217 A * | 12/1998 | Maccecchini | 514/13 |
| 5,854,388 A * | 12/1998 | Harding et al. | 530/329 |
| 5,916,877 A | 6/1999 | Powers et al. | 514/19 |
| 5,959,077 A * | 9/1999 | Fiume et al. | 530/324 |
| 5,994,311 A * | 11/1999 | Eichner et al. | 514/18 |
| 6,001,811 A | 12/1999 | Gyorkos et al. | 514/18 |
| 6,121,243 A * | 9/2000 | Lanzendorfer et al. | 514/28 |
| 6,126,939 A * | 10/2000 | Eisenbach-Schwartz et al. | 424/185.1 |
| 6,420,425 B1 * | 7/2002 | Melman | 514/557 |
| 6,423,688 B1 | 7/2002 | Thorsett et al. | 514/19 |
| 6,673,772 B2 | 1/2004 | Mimoto | 514/19 |
| 6,716,452 B1 | 4/2004 | Piccariello et al. | 424/457 |
| 6,809,186 B1 | 10/2004 | Morseman et al. | 530/409 |
| 2002/0151526 A1 | 10/2002 | Gallop et al. | 514/143 |
| 2003/0181367 A1 | 9/2003 | O'Mahony et al. | 514/12 |
| 2004/0121954 A1 | 6/2004 | Xu | 514/12 |
| 2004/0171555 A1 | 9/2004 | Demuth et al. | 514/18 |
| 2004/0208909 A1 | 10/2004 | Brubaker et al. | 424/424 |

FOREIGN PATENT DOCUMENTS

WO 03/048190 6/2003

* cited by examiner

*Primary Examiner*—David Lukton
(74) *Attorney, Agent, or Firm*—Gifford, Krass, Groh, Sprinkle, Anderson & Citkowski, P.C.

(57) ABSTRACT

A dipeptide or tripeptide carrier system for active agent delivery to cells has an N-terminus natural amino acid and an active agent covalently bonded to a side chain of one of the remaining amino acid bases. The system is amenable to formulation as an oral administrant. The active agent being a therapeutic, a fluorescent dye, or contrast agent where the active agent has a molecular weight of less than 500 atomic mass units. An optional linker is provided intermediate between the active agent and the linking side chain.

16 Claims, 4 Drawing Sheets

SHORT PEPTIDE CARRIER SYSTEM FOR CELLULAR DELIVERY OF AGENT

RELATED APPLICATION

This application claims priority of U.S. Provisional Patent Application Ser. No. 60/524,836 filed Nov. 25, 2003, which is incorporated herein by reference.

FIELD OF THE INVENTION

The present invention generally relates to a short peptide carrier system for delivery of agents to target cells and in particular to a system for delivery of drug or marker agents to intestinal epithelial cells where the agent has undesirably low bioavailability absent the peptide carrier.

BACKGROUND OF THE INVENTION

Delivery of an agent often requires a carrier to get an active agent to target cells. Therapeutic effects in individuals are tied to those in compliance, and therefore oral delivery therapeutics tend to be more effective than injected therapeutics simply owing to better patient compliance with a dosing regime. The formulation of an oral agent is made quite difficult by oral active agent having to traverse strong stomach acid and digestive enzymes found within the gastrointestinal tract. After traversing these impediments, the oral active ingredient then must transport across cellular lipid membranes. While enteric coatings have been used successfully in protecting active agents from stomach acid and enzyme inhibiting adjuvants are suitable to prevent enzymatic degradation, enhancing bioavailability through transport of an active agent across epithelial cell membranes has proven more difficult. Traditional approaches to enhance epithelial cell permeability to an active agent have included compounding with adjuvants such as resorinol, surfactants, polyethylene glycol or bioacids. Alternatively, microencapsulation with liposomes, polysaccharides have also been used to limit enzymatic degradation as well as enhanced permeability.

More recently, active transport of active agents has been investigated to enhance bioavailability of otherwise promising active agents that alone have insufficient movement across epithelial cell membranes, resulting in dosing regimes causing significant side effects. Peptide transport is a specific biochemical process in which small peptides are transported across a membrane by energy dependent saturatable carriers. PEPT1 and PEPT2 are known transporters found in intestinal and renal absorptive epithelial cells.

With an appreciation that peptide transporters are found in intestinal and renal absorptive epithelial cells, attempts have been made to conjugate active agents to peptides, in order to carry active agents through epithelial cell membranes. These efforts have principally focused on coupling an active agent to a C-terminus of a dipeptide in order to enhance affinity. Efforts to attach a dye to the C-terminus of a dipeptide including lysine showed great affinity yet no transport. Abe H. et al., Bioconjug. Chem. 1999; 10:24–31. Other attempts to gain transport of active agents with a dipeptide have involved the use of a D-amino acid coupled to an L-amino acid that in turn is conjugated to a species of interest. Groneberg D. A. et al., Am. J. Physiol. Gastrointest. Liver Physiol. 2001; 281:G697–704. Additionally, a β-amino acid N-terminus has been used to couple to L-lysine which in turn is conjugated to a marker of interest. Otto C. et al., Anat. Rec. 1996; 245:662–7. As a whole, these attempts have met with limited acceptance as a viable active agent carrier system.

In addition to in vivo delivery, a variety of cell culture based systems have been developed to screen for compounds, including the human intestinal cell lines, Caco-2 and HT-29 cells and Madin-Darby canine kidney (MDCK) cells. U.S. Pat. No. 5,856,189 and Walter et al., Journal of Pharmaceutical Sciences, 1996; 85(10):1070 and Veronesi B., Neurotoxicology, 1996 Summer; 17(2):433–43. These cell lines have proven useful to assess permeability of passively absorbed compounds, which do not require a specific transporter for absorption. While these cells do express certain transporters, the expression of these transporters varies with age of cells and growth conditions and consequently these cells are not suitable for testing drugs that target specific transporters.

There are cell-based systems in which specific transporters, including the ileal/renal bile acid transporter and the human renal organic anion transporter 1 (hOAT1), have been expressed and are used to screen for modulators of transport activity with the aim of control of blood cholesterol levels, treatments of diabetes, heart, liver, certain digestive disorders, and assessment of nephrotoxic and nephroprotectant effects as described in U.S. Pat. Nos. 5,869,265 and 6,479,231.

Cultured cell lines of intestinal and renal origin that express PEPT1 and PEPT2 have been identified. (Dantzig et el., Science 1994; 264:430–433; Liang et al., J. Biol. Chem. 1995; 270:6456–6463 and Oh et al., Pharm. Biotechnol. 1999; 12:59–88). With these cultured cell lines, the assessment of short peptide carrier systems for delivery of agents to epithelial cells has been greatly enhanced.

In spite of the existence of cultured cell lines expressing various transporters and chemistries for conjugating an active agent to a short peptide carrier, there still exists a need for an effective short peptide carrier system for cellular delivery of active agents.

SUMMARY OF THE INVENTION

A short peptide carrier system for an active agent delivery to cells includes a dipeptide or tripeptide where the active agent is pendent from a side chain of the intermediate or C-terminus amino acid. The N-terminus peptide is a naturally occurring L-amino acid. The active agent is a small organic molecule therapeutic or spectroscopic marker. A preferred carrier is a dipeptide. More preferably, the peptide carrier has both peptides being L-amino acids. In addition to directly coupling an active agent to the intermediate or C-terminus amino acid side chain, an optional linker of up to a twelve carbon atoms is provided between the peptide side chain and the active agent. With particular active agents, the short peptide carrier system detailed herein serves to stabilize the active agent and facilitate movement across epithelial cell membranes.

A short peptide carrier system for an active agent while suitable for delivery alone is optionally packaged within a microencapsulating agent and/or delivered in conjunction with an adjuvant and a pharmaceutically acceptable excipient.

A method for delivering an active agent to a subject includes administering to the subject a composition including the short peptide carrier system for the active agent as detailed above where the active agent is covalently attached to an intermediate or C-terminus peptide of a dipeptide or tripeptide. The composition is suitable for delivery alone or with a microencapsulating agent thereabout. Additionally, administration also may include an adjuvant and a pharmaceutically acceptable excipient.

BRIEF DESCRIPTION OF THE DRAWINGS

FIG. 3 is a photograph of an electrophoretic gel showing RNA isolated from the same cell lines tested in FIG. 2 that was subjected to RT-PCR (PCR Access system, Promega) using HPEPT1 specific primers (forward primer 342–360, (GCAGTCACCTCAGTAAGCT)    (SEQ ID No: 1)

(GCTGCTGATGTTTGCATA)     (SEQ ID No: 2))

and reverse primer 1575–1592
following standard procedures. The expected hPepT1 PCR fragment is 1.2 kb. The DNA markers are 1 kb and other markers from Invitrogen/Gibco.

DETAILED DESCRIPTION OF THE PREFERRED EMBODIMENTS

The present invention has utility as a system for enhancing the quantity of a small organic molecule active agent able to cross epithelial cell membrane. Without intending to be bound by a particular theory or mechanism, the present invention through use of an N-terminus natural L-amino acid as part of a dipeptide or tripeptide having an active agent covalently bonded to the short peptide carrier through a side chain of the intermediate or C-terminus amino acid greatly enhances the movement of the active agent across epithelial cell membranes. As epithelial cells are most notably found in gastrointestinal tract and renal systems, the present invention enhances bioavailability of orally delivered active agents in particular.

As used herein "subject" is defined to include an individual mammal and specifically includes a human, cow, horse, sheep, dog, cat, rabbit, rat and mouse.

As used herein, an "active agent" is defined to include therapeutic agents such as anti-inflammatories, anti-tumorals, antibiotics, anti-virals, pain medications, steroids, statins, anti-hypertensives and anti-psychotics; fluorescent dye molecules, and contrast agents where the active agent has a molecular weight of less than 500 atomic mass units.

"Natural amino acid" is defined to include amino acids identified in organisms living in a wild state and specifically including sarcosine, ornithine, citrulline, kynurenine, 5-hydroxytryptophan, 3-hydroxykynurenine, 3-aminotyrosine, quisqualic acid, hydroxyproline, as well as N-methylglycine.

As used herein, "synthetic amino acid" is defined to include α-amino acids and β-amino acids that are not natural amino acids and include those known in the peptide chemistry arts for preparing synthetic analogs of naturally occurring peptides, including D and L forms as detailed in U.S. Pat. No. 6,544,951.

A short peptide carrier system for active agent delivery to epithelial cells includes a compound of the formula:

(I)

where $C^a$ is methylene or an L-carbon atom; R is hydrogen or if $C^a$ is methylene then R is methyl; $R^1$ is independently in each occurrence is a side chain of alanine, isoleucine, leucine, methionine, valine, phenylalanine, tyrosine, tryptophan, lysine, threonine, serine, proline, histidine, glutamic acid, glutamine, cysteine, aspartic acid, asparagine, arginine; sarcosine, ornithine, citrulline, kynurenine, 5-hydroxytryptophan, 3-hydroxykynurenine, 3-aminotyrosine, quisqualic acid, or hydroxyproline j is 1 or 2; $C^b$ is a D or L-carbon; $R^2$ and $R^3$ are independently in each occurrence a group consisting of an amino acid side chain and at least one of $R^2$ and $R^3$ has an active agent coupled through an active agent moiety to the side chain; k is 0 or 1; l is 0 or 1 such that j+1 equals 1 or 2; Q is oxygen when l is 0 and Q is NH when l is 1; $C^c$ is a racemic or L-carbon; $R^4$ is a side chain of glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine, hydroxylysine, citrulline, kynurenine, (4-aminophenyl)alanine, 3-(2'-naphthyl)alanine, 3-(1'-naphthyl)alanine, methionine sulfone, (t-butyl)alanine, (t-butyl)glycine, 4-hydroxyphenyl-glycine, aminoalanine, phenylglycine, vinylalanine, propargyl-gylcine, 1,2,4-triazolo-3-alanine, thyronine, 6-hydroxytryptophan, 5-hydroxytryptophan, 3-hydroxykynurenine, 3-aminotyrosine, trifluoromethylalanine, 2-thienylalanine, (2-(4-pyridyl)ethyl)cysteine, 3,4-dimethoxy-phenylalanine, 3-(2'-thiazolyl)alanine, ibotenic acid, 1-amino-1-cyclopentane-carboxylic acid, 1-amino-1-cyclohexanecarboxylic acid, quisqualic acid, 3-(trifluoromethylphenyl)alanine, (cyclohexyl)glycine, thiohistidine, 3-methoxytyrosine, norleucine, norvaline, alloisoleucine, homoarginine, thioproline, dehydroproline, hydroxyproline, homoproline, indoline-2-carboxylic acid, 1,2,3,4-tetrahydroisoquinoline-3-carboxylic acid, 1,2,3,4-tetrahydroquinoline-2-carboxylic acid, α-amino-n-butyric acid, cyclohexylalanine, 2-amino-3-phenylbutyric acid, phenylalanine substituted at the ortho, meta, or para position of the phenyl moiety with one or two of the following groups: a ($C_1$ to $C_4$)alkyl, a ($C_1$ to $C_4$)alkoxy, a halogen or a nitro group, or substituted once with a methylenedioxy group; β-2- and 3-thienylalanine; β-2- and 3-furanylalanine; β-2-, 3- and 4-pyridylalanine; β-(benzothienyl-2- and 3-yl)alanine; β-(1- and 2-naphthyl)alanine; O-alkylated derivatives of serine, threonine or tyrosine; S-alkylated cysteine, S-alkylated homocysteine, the O-sulfate, O-phosphate and O-carboxylate esters of tyrosine; 3-(sulfo)tyrosine, 3-(carboxy)tyrosine, 3-(phospho)tyrosine, the 4-methane-sulfonic acid ester of tyrosine, 4-methanephosphonic acid ester of tyrosine, 3,5-diiodotyrosine, 3-nitrotyrosine, ε-alkyllysine, and delta-alkyl ornithine and halogen substituents containing phenyls therein when the halogen is fluorine, chlorine or bromine; and $R^5$ is hydrogen or a $C_1$–$C_3$ alkyl.

$R^2$ and $R^3$ in at least one occurrence presents a group having a coupling between an active agent and the short peptide carrier backbone. From a preparatory synthesis position, it is preferred carbon $C^b$ has pendent therefrom an amino acid side chain with a chemically reactive heteroatom therein where the heteroatom is oxygen, nitrogen or sulfur. The heteroatom preferably being present as a carboxyl, hydroxyl, amino, amidyl, or mercapto group. In the instance where k is 1 two molecules of the same active agent or two different active agents are optionally delivered across epithelial membrane with a composition according to Formula I. Alternatively, while one of $R^2$ or $R^3$ carries an active agent as a pendent side chain, the other of $R^2$ or $R^3$ optionally includes a charge center at physiological gastrointestinal pH or a side chain to otherwise modify the lipophilicity of an inventive composition. To facilitate transport across epithelial membrane, a side chain incorporating a cationic group such as ammonium, or substituents that increase the overall aliphatic or aromatic character of the inventive composition are preferred. While it is appreciated that the choice of amino acid side chain prior to coupling with an active agent is dependent on factors including the chosen reactive moiety of the active agent, lipophilicity of the active agent, transport characteristics of the dipeptide or tripeptide absent the active agent, and steric effects. Owing to the versatility of reactions available and the comparative stability of the resulting covalent bonds, the amino acid side chain prior to conjugation to an active agent is preferably an amine, carboxylic acid, or an amide. The naturally occurring amino acids, asparagine, aspartic acid, glutamine, glutamic acid and lysine are representative examples. More preferably, the amino acid side chain prior to coupling with the active agent is an amine and lysine represents a more preferred natural amino acid.

The active agent portion of $R^2$ or $R^3$ includes a variety of small molecule therapeutics, fluorescent markers and magnetic contrast agents. It is appreciated that an active agent derivatized to enhance aqueous solution solubility through the formation of salts or the addition of aqueous solution imparting solubility such as sulfonyl groups are preferably used herein as a base compound or one modified to include a reactive moiety. An active agent reactive moiety operative herein illustratively includes an amino, hydroxyl, carboxyl, carbonyl, phosphate, organometallic, mercapto or alkenyl group. Optionally, a linker W is covalently coupled intermediate between the amino acid side chain and active agent reactive moiety of $R^2$ or $R^3$ in order to facilitate synthetic preparation or to modify epithelial membrane transport of an inventive composition. A linker W is chosen to be reactive both with the amino acid side chain and the reactive moiety of the active agent. The linker W has between 0 and 12 carbon atoms in the backbone and illustratively includes dicarboxylic acids, diamines, amino acids, lipids, lectins, saccharides, oligonucleotides and alkylated derivatives thereof, nucleic acids and alkylated derivatives thereof. The linker includes at least two functional groups, the functional groups need not be identical in a particular linker and are each individually chosen from the group of aldehyde, carboxyl, amino, mercapto, hydroxyl, ester, —NCS, and —NCO. In addition to a linker W serving to modify delivery characteristics of an inventive compound, it is appreciated that the linker is optionally provided as an enzymatically cleavable site within $R^2$ or $R^3$ such that the active agent or a further metabolite of the active agent represents a therapeutic entity. In instances where no enzymatic cleavage site exists within $R^2$ or $R^3$, the inventive composition represents an effective therapeutic or spectroscopic marker species.

Regardless of whether a linker W is present or not, a particularly preferred linkage to conjugate an active agent to a short peptide carrier includes the formation of an amide bond between an amine and carboxyl group. This chemistry is well established. This chemistry including the activation of a carboxyl group is well known to the art and includes forming succinimidyl ester which becomes reactive towards the amino group of the carrier peptide.

Methods which are suitable for the preparation of an amide bond are described in Houben-Weyl, Methoden der organischen Chemie (Methods of Organic Chemistry), Volume 15/2; Bodanszky et al., Peptide synthesis, $2^{nd}$ ed. (Wiley & Sons, New York 1976) or Gross, Meienhofer, The Peptides. Analysis, synthesis, biology (Academic Press, New York 1979). Carbodiimides are zero length crosslinkers that mediate the formation of an amide or phosphoramidate linkage between a carboxylate and an amine, or a phosphate and an amine, respectively. Chu, B., Kramer, F. & Orgel, L. (1986), Nucleic Acids Research, 14, 5591–5603. Hoare, D. & Koshland, D. E. (1966) J. Am. Chem. Soc., 88, 2057.) Carbodiimides react with carboxylic acids to form highly reactive O-acylisourea compounds that are short lived and reactive towards nucleophiles to form an amide bond. This reaction works effectively between pH 4.5 and 7.5. Molecules with a phosphate group such as the 5' phosphate on oligonucleotides are reactive with amine-containing groups by using the carbodiimide reaction.

The following methods are preferably used herein: active ester method using N-hydroxy-succinimide or 1-hydroxybenzotriazole as the ester component, coupling with a carbodiimide, such as dicyclohexylcarbodiimide, or with propanephosphonic anhydride and the mixed anhydride method using pivaloyl chloride.

The preparation of the optically active amines, used as starting compounds, is carried out starting from optically active α or β-amino acids, the center of asymmetry thereof being retained. For this, an N-protected amino acid aldehyde is prepared in a known manner and is coupled to a corresponding heteroarylalkyl unit in an aldol-analogous addition to give, after splitting off of the N-protective group, aminoalcohol. Diastereomer mixtures in respect of the center carrying OH are obtained and are resolved in a manner which is known per se, for example by fractional crystallization or by chromatography. The diastereomer purity is checked by means of high performance liquid chromatography, and the enantiomer purity can be checked in a known manner by conversion into Mosher derivatives. Mosher H. S. et al., J. Org. Chem. 1969; 34:2543.

To the compound obtained, including the polymeric carrier, a styrene-divinylbenzene copolymerisate and a coupling substance, is attached to the carboxy-terminal amino acid of the peptide or peptide fragment to be synthesized. The carboxy-terminal amino acid carrying its amino group is in protected form, and is attached via ester formation. The masking group for the amino function is preferentially of the kind that can be cleaved under basic conditions, i.e. by treatment with a base. The esterification is effected by known methods via activation of the carboxyl group.

Thus the carboxyl group can for example be converted to an acid azide, anhydride, imidazolide, isoxazolide or an activated ester, or through reaction with a carbodiimide such as N,N'-dicyclohexylcarbodiimide (DCC) to an O-acylisourea. The most commonly used mode is to use a carbodiimide and a catalyst such as 4-dimethylaminopyridine or N-hydroxysuccinimide. E. Wunsch: Synthese von Peptiden, Georg Thieme Verlag, Stuttgart 1974 in Houben-Weyl: Methoden der Org. Chemie, 15/I and II, $4^{th}$ edition.

Synthesis of the polymeric carrier by standard peptide synthetic procedures are described in U.S. Pat. No. 4,914,151. The amino acid or peptide fragment carrying an amino protecting group is coupled to the polymeric carrier resin using such as dicyclohexyl carbodiimide and 4-aminopyridine within 2 to 24 hours, preferably within 12 hours at a temperature of 0° to 50° C., preferably at a temperature of 20° to 25° C., in a solvent such as dichloromethane or dimethylformamide or a mixture of both.

If the amino acid to be condensed, as well as those to be condensed thereafter, bears a functioned group in the side chain, such as a carboxy-, amino-, amido-, hydroxy-, mercapto or guanidino-function, the latter is preferentially protected by such a group, that is resistant to the cleavage reaction of the peptide or fragment from the carrier resin at a later stage. The specific purpose to be achieved determines the appropriate selection of the protection groups for the side chain functions.

A carboxyl-protecting group is one which is commonly used in peptide chemistry. Such groups are cleavable under mild reaction conditions so as to prevent undesirable side reactions. Examples of such carboxylic acid protecting groups illustratively include t-butyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-trimethoxytrityl, 2-phenylpropyl, trimethylsilyl, t-butyldimethylsilyl, phenacyl, 2,2,2-trichloroethyl, β-(trimethylsilyl)ethyl, β-(di(n-butyl)methylsilyl) ethyl, p-toluenesulfonylethyl, 4-nitrobenzylsulfonylethyl, allyl, cinnamyl, 1-(trimethylsilylmethyl)propenyl and like moieties. The species of carboxy-protecting group employed is not critical so long as the derivatized carboxylic acid is stable to the conditions of subsequent reaction(s) and can be removed at the appropriate point without disrupting the remainder of the molecule. Further examples of these groups are found in C. B. Reese and E. Haslani, "Protective Groups in Organic Chemistry," J. G. W. McOmie, Ed., Plenum Press, New York, N.Y., 1973, Chapter 5, respectively, and T. W. Greene and P. G. M. Wuts, "Protective Groups in Organic Synthesis," $2^{nd}$ ed., John Wiley and Sons, New York, N.Y., 1991, Chapter 5. The cleavage can be effected by solvolysis in acidic or basic medium, by hydrogenolysis, reduction, photolysis or also under physiological conditions. As a rule the carboxyl protection group is replaced by hydrogen. Protecting groups of this kind and their cleavage are described in "Protective Groups in Organic Chemistry", Plenum Press, London, New York, N.Y., 1973 and in "The Peptides", Vol. I, Schroder and Lubke, Academic Press, London, New York, N.Y., 1965, as well as in "Methoden der Organischen Chemie", Houben-Weyl, 4. Auflage, Bd. 15/1, Georg Thieme Verlag, Stuttgart, 1974. In this synthesis method carboxyl groups can be protected, such as by esterification. Especially suited for this reaction are lower, substituted alkanols such as 2,2,2-trichloroethanol, t-butanol, benzoylmethanol or benzyl alcohol. Specially preferred groups are the t-butyl group and the benzyl group.

A protecting group for a hydroxyl function also may prove useful in the practice of the present invention. Examples of hydroxyl protecting groups illustratively include tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl, 2,2,2-trichloroethoxycarbonyl, and the like.

Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3. A preferred hydroxy-protecting group is the tert-butyl group.

A protecting group for the amino function can be an acyl group, such as an acyl of an aliphatic, aromatic or araliphatic carboxylic acid, especially lower alkanoyl such as acetyl or propionyl, or aroyl such as benzoyl, or formyl or an acyl of a carbonic acid half-ester, such as benzyloxycarbonyl or fluorenylmethyloxycarbonyl (Fmoc). Examples of amino-protecting groups illustratively include the formyl ("For") group, the trityl group, the phthalimido group, the trichloroacetyl group, the trifluoroacetyl group, the chloroacetyl, bromoacetyl, and iodoacetyl groups, urethane-type protecting groups, such as t-butoxycarbonyl ("t-Boc"), 2-(4-biphenylyl)propyl-2-oxycarbonyl ("Bpoc"), 2-phenylpropyl-2-oxycarbonyl ("Poc"), 2-(4-xenyl)isopropoxycarbonyl, 1,1-diphenylethyl-1-oxycarbonyl, 1,1-diphenylpropyl-1-oxycarbonyl, 2-(3,5-dimethoxyphenyl)propyl-2-oxycarbonyl ("Ddz"), 2-(p-toluyl)propyl-2-oxycarbonyl, cyclopentanyloxycarbonyl, 1-methylcyclopentanyloxycarbonyl, cyclohexanyloxycarbonyl, 1-methyl-cyclohexanyloxycarbonyl, 2-methylcyclohexanyl-oxycarbonyl, 2-(4-toluylsulfonyl)ethoxycarbonyl, 2-(methylsulfonyl) ethoxycarbonyl, 2-(triphenylphosphino)-ethoxycarbonyl, 9-fluorenylmethoxycarbonyl ("Fmoc"), 2-(trimethylsilyl) ethoxycarbonyl, allyloxycarbonyl, 1-(trimethylsilylmethyl)

prop-1-enyloxycarbonyl, 5-benzisoxalylmethoxycarbonyl, 4-acetoxybenzyl-oxycarbonyl, 2,2,2-trichloroethoxycarbonyl, 2-ethynyl-2-propoxycarbonyl, cyclopropylmethoxycarbonyl, isobornyloxycarbonyl, 1-piperidyloxycarbonyl, benzyloxycarbonyl ("Cbz"), 4-phenylbenzyloxycarbonyl, 2-methylbenzyloxycarbonyl, α-2,4,5,-tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy)benzyloxycarbonyl and the like; the benzoylmethylsulfonyl group, the 2,2,5,7,8-pentamethylchroman-6-sulfonyl group ("PMC"), the dithiasuccinoyl ("Dts") group, the 2-(nitro)phenyl-sulfenyl group ("Nps"), the diphenylphosphine oxide group, and like amino-protecting groups. The species of amino-protecting group employed is not critical so long as the derivatized amino group is stable to the conditions of the subsequent reaction(s) and can be removed at the appropriate point without disrupting the remainder of the molecule. Preferred amino-protecting groups are Boc, Cbz and Fmoc. Further examples of amino-protecting groups embraced by the above term are well known in organic synthesis and the peptide art and are described by, for example, T. W. Greene and P. G. M. Wuts, "Protective Groups in Organic Synthesis," $2^{nd}$ ed., John Wiley and Sons, New York, N.Y., 1991, Chapter 7; M. Bodanzsky, "Principles of Peptide Synthesis," $1^{st}$ and $2^{nd}$ revised Ed., Springer-Verlag, New York, N.Y., 1984 and 1993; and J. M. Stewart and J. D. Young, "Solid Phase Peptide Synthesis," $2^{nd}$ Ed., Pierce Chemical Co., Rockford, Ill., 1984; E. Atherton and R. C. Shephard, "Solid Phase Peptide Synthesis—A Practical Approach" IRL Press, Oxford, England (1989).

The cleavage of such an acyl residue serving as protecting group from an amino function can be performed by known methods, such as solvolysis exemplified by alcoholysis. Moreover it can be brought about by hydrolysis in acidic or basic medium. The alcoholytic cleavage of an acyl residue can be effected, such as in presence of a basic reagent and/or at elevated temperature, e.g. from 50° C. to 120° C. with a lower alkanol such as n-butanol or ethanol. A base is used such as an alkali metal alcoholate, such as sodium or potassium ethoxide or an alkali metal hydroxide, such as sodium or potassium hydroxide.

Other aminoprotecting groups, such as lower alkoxycarbonyl-groups e.g. t-butoxycarbonyl, are cleaved under mild acidic conditions, such as by treatment with trifluoroacetic acid. Another group, cleavable under especially mild conditions is an ethoxycarbonyl group carrying in the β-position a silyl group substituted with three hydrocarbon residues, such as triphenylsilyl, dimethyl-butylsilyl or especially trimethylsilyl. These are cleaved by reaction with fluoride ions, especially fluoride salts of quaternary ammonium bases, such as tetraethylammonium fluoride.

An especially suitable protecting group for the α or β-amino group of the amino acids to be attached to the resin-linker and subsequently to the growing peptide chain is the 9-fluorenylmethyloxycarbonyl (Fmoc) group. Fmoc is cleaved with bases such as alkali hydroxides or carbonates, as well as especially mildly with organic bases such as piperidine.

For protection of side-chain amino (ε-amino) groups any group commonly used in peptide chemistry can be applied. However, in view of the necessity to cleave groups from α or β-amino functions for the propagation of the synthetic sequence it is desirable to choose such groups that are not cleaved when the amino protecting group is split off. For example, if a group is used for amino protection that can be removed by base treatment such as the Fmoc-group, then preferentially a group is employed for side chain amino groups which can be removed upon completion of the synthesis by acidic treatment. For protection of side chain hydroxyl groups all protecting groups conventionally known to be useful in the peptide field can be used, as detailed in Houben-Weyl, above. These groups are preferably groups cleavable by acidolysis. These groups illustratively include 2-tetrahydropyranyl and especially t-butyl and t-butoxycarbonyl. Groups that are cleavable by reduction are also operative herein, such as benyzl and benzyloxy carbonyl or acyl such as acetyl or benzoyl, optionally substituted. These reductive groups can be removed by solvolysis or hydrogenolysis.

For protection of side chain mercapto groups all usual protecting groups of the peptide field can be applied. In particular the mercapto groups can be blocked by acylation, alkylation or disulfide formation. Preferred mercapto-protecting groups are, for example, benzyl, optionally substituted in the phenyl radical, for example by methoxy or nitro, such as 4-methoxy benzyl, diphenylmethyl optionally substituted in the phenyl moiety, for example by methoxy, such as 4,4-dimethoxy-diphenylmethyl, triphenylmethyl, trimethylethyl, benzylthiomethyl, tetrahydropyranyl, acylaminomethyl, benzoyl, benzyloxycarbonyl or aminocarbonyl, such as ethylaminocarbonyl.

For protection of side chain carboxylic acid amide groups such as occurring in asparagine and glutamine the groups known and commonly used in peptide chemistry may be applied. Particularly such protection is provided by alkylation at the N-atom of the amide function with methoxy-substituted benzyl diphenylmethyl or xanthyl groups all removable by acidolysis in presence or absence of a scavenger such as anisol.

The guanidino group such as occurring in the side chain of arginine is likewise protected by methods known in the art of peptide synthesis. See, e.g. "Protective groups in Organic Chemistry", Plenum Press, London, New York N.Y. (1973). The protecting groups used here include tosyl, p-methoxybenzenesulfonyl, 4-methoxy-2,3,6-trimethylbenzenesulfonyl, mesitylenesulfonyl, carbobenzoxy and t-butoxy carbonyl groups. Deblocking is performed by acidolysis or hydrogenation.

An active agent according to the present invention is virtually unlimited provided the molecular weight and hydrophilicity of the active agent do not compromise the ability of inventive short peptide carrier to traverse epithelial cell membrane. Active agents operative herein as therapeutics illustratively include anti-neoplastic compounds such as floxuridine, gemcitabine, cladribine, dacarbazine, melphalan, mercaptopurine, thioguanine, cis-platin, and cytarabine; and anti-viral compounds such as fludarabine, cidofovir, tenofovir, and pentostatin. Further examples of pharmaceutical species according to the invention illustratively include adenocard, adriamycin, allopurinol, alprostadil, amifostine, aminohippurate, argatroban, benztropine, bisphosphinate, bortezomib, busulfan, calcitriol, carboplatin, daunorubicin, dexamethasone, topotecan, docetaxel, dolasetron, doxorubicin, epirubicin, estradiol, famotidine, foscarnet, flumazenil, fosphenytoin, fulvestrant, hemin, ibutilide fumarate, irinotecan, levocarnitine, idamycin, sumatriptan, granisetron, metaraminol, metaraminol, methohexital, mitoxantrone, morphine, nalbuphine hydrochloride, nesacaine, oxaliplatin, palonosetron, pamidronate, pemetrexed, phytonadione, ranitidine, testosterone, tirofiban, toradol, triostat, valproate, vinorelbine tartrate, visudyne, zemplar, zemuron, and zinecard.

Active agents operative as fluorescent marker molecules illustratively include: coumarins such as 4-methyl-3-coumarinylacetic acid, 3-Acetamidocoumarin, 7-Carboxymethoxy)-3-chloro-4-methylcoumarin, 7-(Diethylamino)coumarin-3-carboxylic acid, 7-Hydroxycoumarin-3-carboxylic acid, 7-Hydroxy-4-methyl-3-coumarinylacetic acid, 7-Methoxycoumarin-3-carboxylic acid; cyanine dyes such as those disclosed in U.S. Pat. No. 5,986,086; and other fluorescent dye species as disclosed in U.S. Pat. No. 6,821,952.

An active agent operative herein as a contrast agent illustratively includes those disclosed in U.S. Pat. No. 6,610,269.

While a variety of reactive moieties found on the active agent are suitable for coupling an active agent to an amino acid side chain of $R^2$ or $R^3$, either directly or through an optional linker W, it is preferred that the active agent reactive moiety not be an alcohol group or an amine group even though these are appreciated to be operative herein.

According to the present invention, the amino acid including side chain $R^1$ is a naturally occurring L-amino acid. More preferably, $R^1$ is one of the aliphatic amino acids namely, alanine, leucine, isoleucine, and valine. While not intending to be limited to a particular hypothetical mechanism for epithelial cell membrane transport, it is believed that an aliphatic naturally occurring amino acid at the N-terminus of an inventive short peptide carrier system is a recognition site for active transport by PepT1 and possibly PepT2. Most preferably, $R^1$ is an alanine (methyl) side chain.

While an inventive composition is a dipeptide or tripeptide, in a preferred embodiment an inventive composition is a dipeptide and j is preferably 1. In order to satisfy the requirement that the N-terminus amino acid is a naturally occurring amino acid, $C^a$ in Formula I is either a methylene (glycine) or a levorotary (L) steroisomeric carbon atom. Preferably, $C^a$ is a levorotary carbon atom center. More preferably, $C^b$ and $C^c$, if present, are also both levorotary carbon atoms. In a still more preferred embodiment, k is 0, 1 is 0, and Q is an oxygen atom.

An inventive composition is readily formulated and administered to treat a variety of conditions or identify cells that have uptaken the inventive composition containing an appropriate marker or contrast agent as the active agent. The inventive composition is administered by any conventional means available for use in conjunction with pharmaceuticals, either as individual ingredients or in a combination of other therapeutic active ingredients. The inventive composition is administered alone, or with a pharmaceutical carrier selected on the basis of the chosen route of administration and standard pharmaceutical practice.

A dosage for an inventive composition is determined for the chosen use, including the condition to be treated or the sensitivity of the dye, the therapeutic active agent used to treat the condition and the type of subject treated, including considerations as to age, weight, and sex.

The dosage for an inventive composition is a therapeutically effective amount of active agent and varies depending upon known factors such as the pharmacodynamic characteristics of the particular active ingredient and its mode and route of administration; age, sex, health and weight of the recipient; nature and extent of symptoms; kind of concurrent treatment, frequency of treatment and the effect desired. A typical daily dosage of active agent is from 1 to 400 milligrams per kilogram of body weight. Ordinarily, 1 to 200, and preferably 1 to 50, milligram per kilogram per day given in divided doses 2 to 4 times a day or in sustained release form is effective to obtain desired results.

Dosage forms suitable for internal administration contain from about 1.0 to about 500 milligrams of active ingredient per unit. In these pharmaceutical compositions, the active ingredient is typically present from 0.05–95% by weight based on the total weight of the dose.

Administration may be by any means suitable for the condition to be treated and may include, for example, oral administration. For example, oral administration is optionally accomplished using solid dosage forms such as capsules, tablets and powders, or in liquid dosage forms such as elixirs, syrups, emulsions and suspensions. The inventive composition is, for example, parenterally administered by injection, rapid infusion, nasopharyngeal adsorption, or dermoabsorption. The inventive composition also is optionally administered intramuscularly, intravenously, or as a suppository.

Gelatin capsules may contain inventive composition and powdered carriers such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration optionally contain coloring and flavoring to increase patient acceptance.

In general, water, a suitable oil, saline, aqueous dextrose, and related sugar solutions and glycols are suitable carriers for parenteral solutions. Solutions for parenteral administration may contain suitable stabilizing agents and, if necessary, buffer substances. Antioxidizing agents such as sodium bisulfate, sodium sulfite or ascorbic acid either alone or combined are suitable stabilizing agents. Citric acid and its salts and sodium EDTA are also operative herein as stabilizing agents. In addition, parenteral solutions optionally contain preservatives such as benzalkonium chloride, methyl- or propyl-paraben and chlorobutanol. Suitable pharmaceutical carriers are descried in Remington's Pharmaceutical Sciences, 20th edition are operative herein.

Additionally, standard pharmaceutical methods can be employed to control the duration of action. These illustratively include control release preparations and can include appropriate macromolecules, for example polymers, polyesters, polyaminoacids, polyvinylpyrrolidone, ethylenevinylacetate, methyl cellulose, caraboxymethyl cellulose or protamine sulfate. The concentration of macromolecules as well as the methods of incorporation can be adjusted in order to control release. Additionally, the inventive composition can be incorporated into particles of polymeric materials such as polyesters, polyaminoacids, hydrogels, poly (lactic acid) or ethylenevinylacetate copolymers. In addition to being incorporated, the inventive composition optionally is also used to trap the compound in microcapsules.

Suitable exemplary dosage forms for administration of the inventive composition follow.

Capsules are prepared by filling standard two-piece hard gelatin capsulates each with 100 milligram of powdered active ingredient, 175 milligrams of lactose, 24 milligrams of talc and 6 milligrams magnesium stearate.

A soft gelatin capsule includes mixture of active ingredient in soybean oil is prepared and injected by means of a positive displacement pump into gelatin to form soft gelatin capsules containing 100 milligrams of the active ingredient. The capsules are then washed and dried.

Tablets are prepared by conventional procedures so that the dosage unit is 100 milligrams of active ingredient. 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or to delay absorption.

A parenteral inventive composition suitable for administration by injection is prepared by stirring 1.5% by weight of active ingredients in 10% by volume propylene glycol and water. The solution is made isotonic with sodium chloride and sterilized.

An aqueous suspension of an inventive composition is prepared for oral administration so that each 5 millimeters contain 100 milligrams of finely divided active ingredient, 200 milligrams of sodium carboxymethyl cellulose, 5 milligrams of sodium benzoate, 1.0 grams of sorbitol solution U.S.P. and 0.025 millimeters of vanillin.

As an encapsulated particulate, active particles of an inventive composition are prepared from a polymer using a coacervation method, with a particle size is between about 5 nm and 750 microns, more preferably between about 10 nm and 500 microns and most preferably between about 50 nm and 800 nm. An inventive composition is complexed to the particles using various methods known to those skilled in the art.

A general method for preparation of such particles is detailed in U.S. 2003/0181367 A1.

In order to demonstrate efficacy of an inventive composition, an inventive composition is used in a cell-based screening system embodiment that includes a cell line that is engineered to express a transporter (TR) that is normally expressed in the intestine of mammals and a marker molecule that is transported by the specific transporter (TR). This embodiment has utility in that it allows for rapid and reproducible screening of a wide variety of molecules for their ability to bind to a given intestinal transporter. The binding of a molecule is the first step and is a necessary step to ultimate transport of the compound. By screening for binding to the transporter, it is possible to efficiently test for a required step in absorption. The transporters, according to the present invention, are any intestinal mammalian transporter. Representative intestinal mammalian transporters and compounds that are known to interact with specific transporters are shown in Table 1.

TABLE 1

Representative Intestinal Transporters and Substrates Therefor

| Transporters | Active Species/Substrates |
|---|---|
| Amino acid transporters | gabapentin, isobutyl gaba, L-methyldopa, L-dopa |
| Peptide transporter (HPEPT1, HPT1) | β-lactam antibiotics, ACE inhibitors, valacyclovir, valganciclovir, L-methyldopa, cephalexin |
| Nucleoside transporters (CNT1 CNT2, ENT1 ENT2) | zidovudine, zalcitabine cladribine ara-C, ara-A, fludarabine, cladribine, dilazep, dipyridamole, draflazine hypoxanthine |
| Organic cation transporters (OCT1, ORCTL3) | tetraethylammonium, N-methylnicotineamide, thiamine, tyramine, tryptamine, choline, spermine, spermidine, d-tubocurarine, procanamide, dobamine, noradrenaline, serotonin, istamine, corticosterone, MPP, despramine, qunidine, verapamil, midazolam |
| Organic anion transporters (MOAT (MRP2), MCT1) | methotrexate, cefodizime, ceftriaxone, pravastatin, temocaprilat, salicylic acid, p-amnobenzoic acid, benzoic acid, nicotinic acid, lactate |
| Glucose transporters (GLUT2, GLUT5, SGLT1, SAAT1) | p-nitrophenyl-β-?D-glucopyranoside, β-D-galactopyranoside |
| Bile acid transporters (IBAT/ISBT) | thyroxine, chlorambucil, crilvastatin |
| Phosphate transporters (NPT4, NAPI-3B) | fosfomycin, foscarnet, digoxin, cyclosporin |
| Vitamin transporters (SVCT1-2, folate transporters, SMVT) | reduced vitamin C, methotrexate, nicotinic acid, thiamine, vitamin B-12, R.I.-K(biotin)-Tat9 |

A cell line operative in an inventive system displays adherent growth, is readily transfectable, and shows low endogenous transport activity. An exemplary, non-limiting, list of suitable cell lines is given in Table 2.

TABLE 2

Potential Cell Lines

| Cell Lines | Source/Characteristics |
|---|---|
| $D_{par}$ | Subclone of DAOY; a human medulloblastoma cell line |
| CHO | Biopsy from an ovary of an adult Chinese hamster |
| HeLa | Derived from human cervical adenocarcinoma |
| Vero | Derived from kidney of a normal adult African green monkey |
| NIH/3T3 | Established from NIH Swiss mouse embryo cultures |

An inventive marker molecule operative in an inventive system is a substrate for a respective transporter such that marker transport across the cellular membrane is dependent upon the respective target transporter. An inventive marker molecule is of natural or synthetic origin. Preferably, a marker molecule is radiolabeled or has fluorescent properties or the ability to subsequently bind a detectable moiety.

It is appreciated that these methods of marker molecule assay and a number beyond those described herein are conventional to the art.

The example presented below is intended to illustrate a particular embodiment of the invention and is not intended to limit the scope of the specification, including the claims, in any way.

EXAMPLE 1

Figure 1:
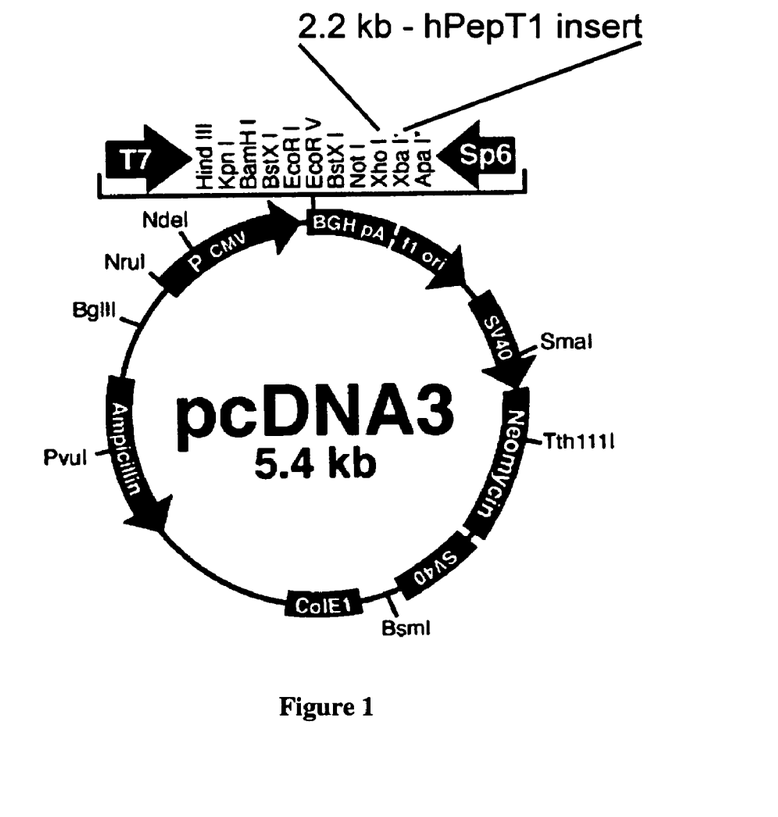
FIG. 1 is a schematic showing the plasmid vector containing the cloned HPEPT1 gene that is operative to transfect the $D_{par}$ cell line to form the DC5 cell line that constitutively overexpresses the HPEPT1 transporter.
Figure 2:
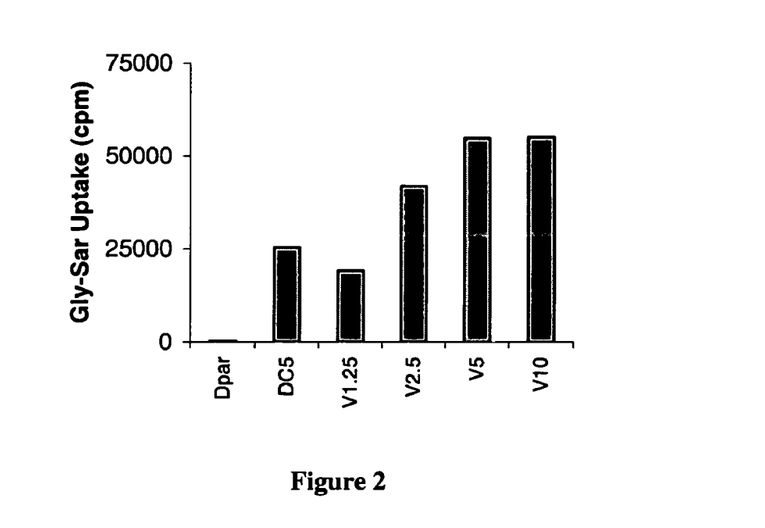
FIG. 2 is a graph showing the uptake of the model dipeptide, $^3$H-Gly-Sar in the DC5 cell line and the comparative parental cell line, $D_{par}$. Also shown, as a positive control, is uptake of the $^3$H-Gly-Sar in the parental cell line infected with Ad.hpept1, a recombinant adenovirus that contains the hpept1 gene, at concentrations of 1,250 (V1.25), 2,500 (V2.5), 5,000 (V5) or 10,000 (V10) viral particles/cell.
Figure 3:
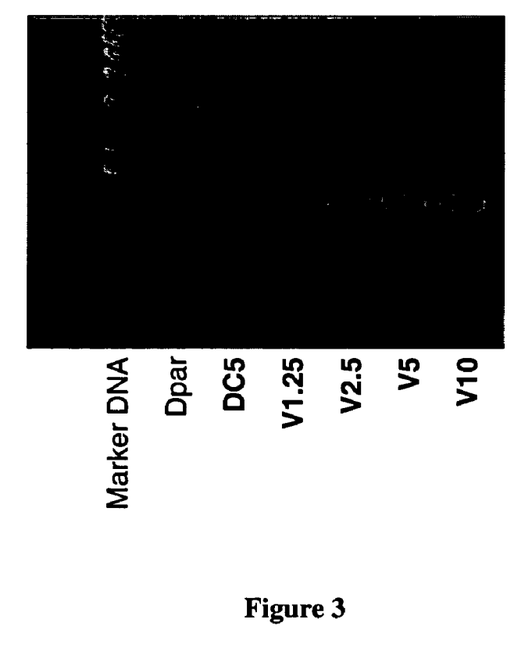

A human medulloblastoma cell line ($D_{par}$) was engineered to overproduce hpept1 using a eukaryotic expression plasmid containing the hPept1 gene. A schematic of the expression plasmid is shown in FIG. 1. The engineered cell line, termed DC5, is measured by a functional uptake assay of the marker dipeptide $^3$H-Gly-Sar. FIG. 2 is a graph showing the uptake of the model dipeptide $^3$H-Gly-Sar in the DC5 and the parental cell line $D_{par}$. Also shown, as a positive control, is uptake of the $^3$H-Gly-Sar in the parental cell line infected with Ad.hpept1, a recombinant adenovirus that contains the hpept1 gene, at concentrations of 1,250 (V1.25), 2,500 (V2.5), 5,000 (V5) or 10,000 (V10) viral particles/cell. DC5 also shows high levels of expression of the hpept1 transporter as measured by reverse transcriptase mediated polymerase chain reaction (RT-PCR). FIG. 3 is a digital photograph of the RNA isolated from the same cell lines tested in FIG. 2 that was subjected to RT-PCR (PCR Access system, Promega) using HPEPT1 specific primers (forward primer 342–360,

```
(GCAGTCACCTCAGTAAGCT)     (SEQ ID No: 1)

(GCTGCTGATGTTTGCATA)      (SEQ ID No: 2))
``` and reverse primer 1575–1592 following standard procedures. The expected hPepT1 PCR fragment was 1.2 kb. The markers are 1 kb plus markers from Invitrogen/Gibco.

The developed system functions as an initial screen for interaction with the dipeptide transporter by measuring the ability of a given test compound to inhibit the uptake of the marker dipeptide $^3$H-Gly-Sar. Using this system in a 96-well format, one can rapidly screen compounds for their ability to bind to the dipeptide transporter by measuring the inhibition constant ($K_i$) of the compound against Gly-Sar uptake. In this assay, a positive result indicates binding, but not necessarily transport. Positive results are assessed for actual transport in conventional uptake assays.

As an example, a group of cephalosporin analogs were used to inhibit the uptake of $^3$H-Gly-Sar. The cephalosporin compounds have long been recognized as substrates for hpept1. Oh, D., P. Sinko, and G. Amidon, International Journal of Pharmaceutics, 1992. 85: p. 181–187.

Figure 4:
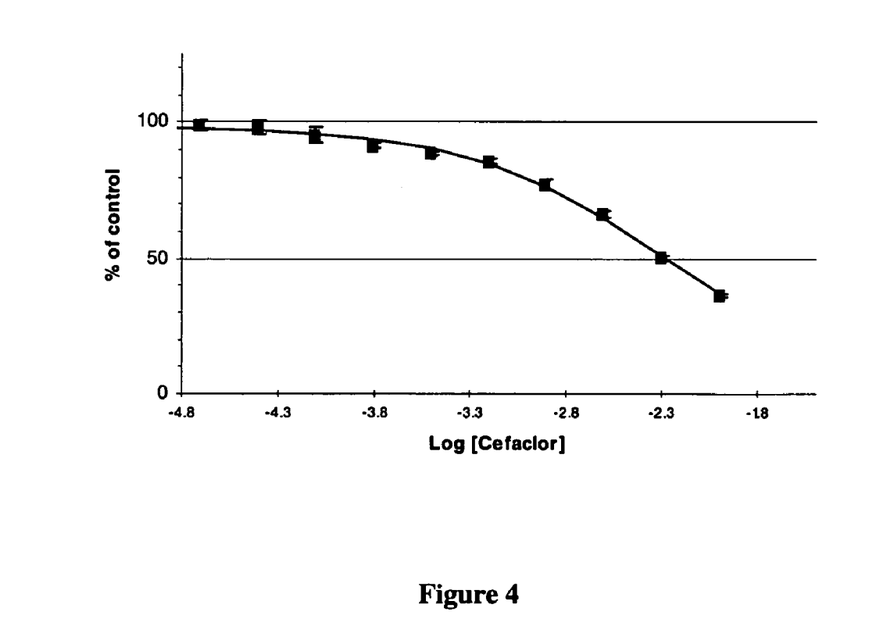
FIG. 4 is a graph that illustrates how the DC5 cell line can be used to determine the inhibition constant ($K_i$) for cefaclor relative to $^3$H-Gly-Sar.

As seen in the FIG. 4, the $K_i$ for a given compound, in this case Cefaclor, is determined in DC5 cell line by measuring the uptake of $^3$H-glycine-sarcosine (GS) in the presence of a range of concentrations of the test compound Cefaclor. The inhibitory $K_i$ for a given compound is determined in DC5 cell line using the radioactive substrate 3H-glycine-sarcosine (GS). DC5 cells were plated (12,000 cells/well) in 96-well tissue culture plates (Falcon) and allowed to grow for 2 days. The cells were washed once with 200 ul of uptake buffer and aspirated. The plates were cooled to 4° C. and 25 ul of uptake buffer containing 50 uM Gly-Sar (0.5 uCi/ml) was added. The uptake buffer also contained the test β-lactam antibiotic, Cefaclor, over a range of concentrations. Uptake was initiated by placing the plate in a shaker water bath (37° C.) and terminated at 10 min by rapid washing with multiple changes of 4° C. PBS (Sigma). The radioactive peptide was extracted from the cell layer with 200 ul of methanol:water (1:1) and counted in 4 ml of CytoScint ES™ scintillation cocktail (ICN). Non-linear regression analysis of the data was used to determine the $IC_{50}$ using the solver function in Microsoft Excel spreadsheets. In Table 3 is shown the $K_i$ determination for a variety of cephalosporin drugs. The data show a range of Ki values for the cephalosporin drugs and a distinct demarcation between those that are well absorbed (e.g., high bioavailability) and those that are not well absorbed. Under these conditions, it is concluded that those compounds showing a $K_i$ below approximately 10–11 mM have the potential to be well absorbed and further testing is warranted.

TABLE 3

| Ki values for cephalosporin compounds determined in the DC5 cell line | | |
|---|---|---|
| Compound | TSRL - Ki | Bioavailability[1] |
| Cefadroxil | 2.7 | 100 |
| Cefaclor | 5.39 | 100 |
| Cephradine | 7.02 | 100 |
| Cephalexin | 11.37 | >95 |
| Cephalothin | 11.07 | <5 parenteral |
| Cefamandole | 16.35 | <1 parenteral |
| Ceftriaxon | >20 | <5 parenteral |
| Cefuroxime | 23.2 | <1 parenteral |

[1]Bretschneider, B., M. Brandsch, and R. Neubert, Intestinal transport of beta-lactam antibiotics: analysis of the affinity at the H+/peptide symporter (PEPT1), the uptake into Caco-2 cell monolayers and the transepithelial flux. Pharm Res, 1999. 16(1): p. 55–61.

EXAMPLE 2

Synthesis of L-Ala-Lys-Nε-AMCA in Solution

Z-L-Ala-Lys (34.9 mg) is dissolved in an aqueous $Na_2CO_3$ solution (21.28 mg/ml). AMCA-ONSu (20 mg), dissolved in dimethyl formamide (1 ml), is added and the mixture stirred for one hour. The mixture is diluted with 2 ml distilled water and applied to a Zorbex C18 column. The protected title compound is eluted with sequentially with water and 50% methanol. Fractions containing the protected title compound are pooled. After evaporation of the solvent, the protective Z group is removed (platinum and hydrogen gassing) and the labeled peptide purified by using a reverse-phase C18 HPLC silica gel column with 0.1% trifluoroacetic acid(TFA)-$H_2$O-acetonitrile.

EXAMPLE 3

Synthesis of L or D-Ala-Lys-Nε-AMCA by SPPS

Solid phase peptide synthesis (SPPS) on Wang resin using Fmoc-chemistry is adopted for the synthesis of the dipeptide. After conjugation of AMCA to the side-chain amino group of Lys, the labeled peptide is cleaved off with TFA-EDT-phenol to obtain the crude product. The product is purified by using reverse-phase C18 HPLC silica gel column with 0.8% TFA-$H_2$O-Acetonitrile. After purification, the fractions with the dipeptide-AMCA conjugate are lyophilized.

EXAMPLE 4

Synthesis of L-Lys-Nε-AMCA

Boc-Lys (3.73 mg) is dissolved in dimethyl formamide (0.62 ml) and mixed with AMCA-ONSu (5 mg) in dimethyl formamide (0.5 ml). The mixture is allowed to react at room temperature for 1 hour. The product is lyophilized. 1 ml of trifluoroacetic acid is added for one hour to deprotect the amino acid. The product is lyophilized again and the labeled amino acid is purified by using a reverse-phase C18 HPLC silica gel column with 0.1% TFA-H$_2$O-acetonitrile.

EXAMPLE 5

Figure 5:
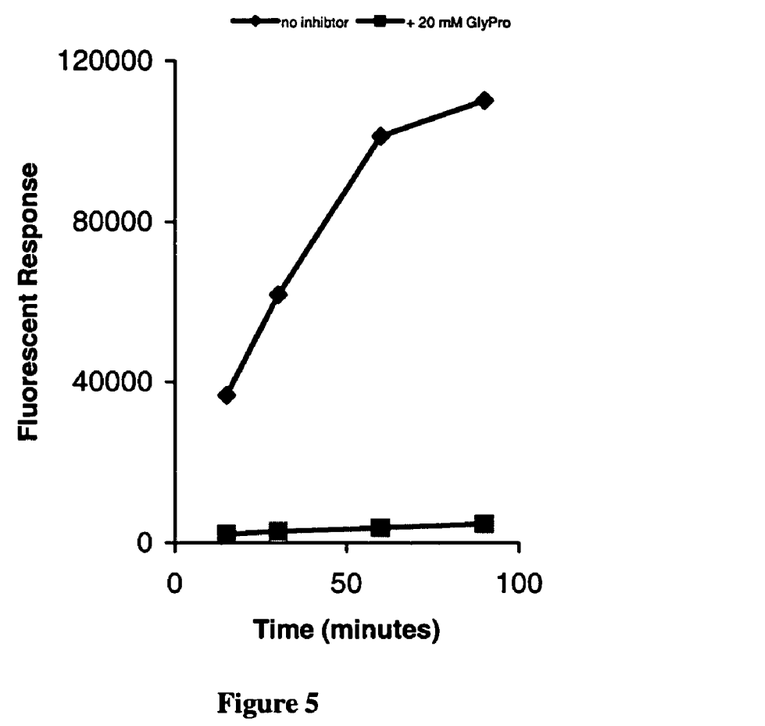
FIG. 5 is a graph showing the inhibition of LALA uptake into the DC5 cell line with the competitive substrate Glycine-Proline (Gly-Pro).
Figure 6:
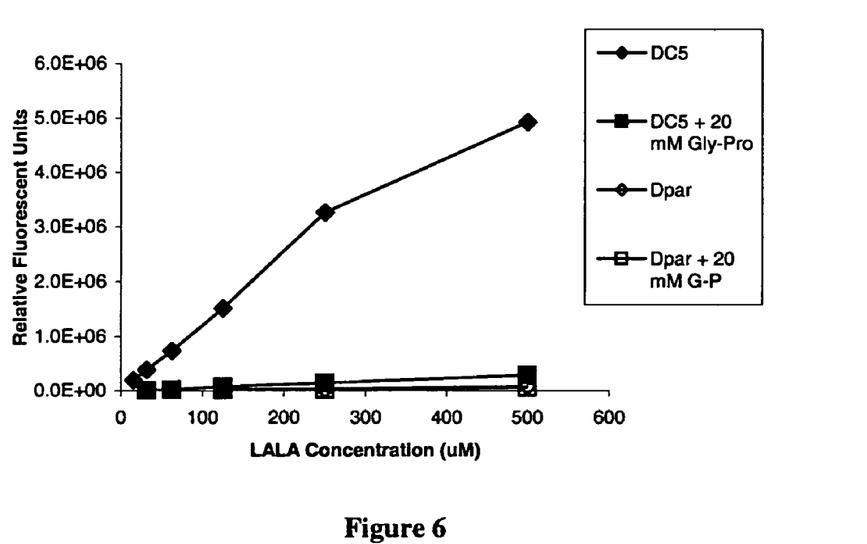
FIG. 6 is a graph showing the uptake of LALA in DC5 and $D_{par}$ as a function of LALA concentration. DC5 and $D_{par}$ cells are incubated in transport buffer and the indicated concentrations of LALA added (♦) and (|), respectively. These experiments are repeated in the presence of 20 mM Gly-Pro for DC5 (♥) and $D_{par}$ (?). After 30 minutes, the cells are washed and processed for fluorescent determination. LALA is specifically taken up in the DC5 and not the parental cell line $D_{par}$. This uptake is specifically inhibited by Gly-Pro.
Figure 7:
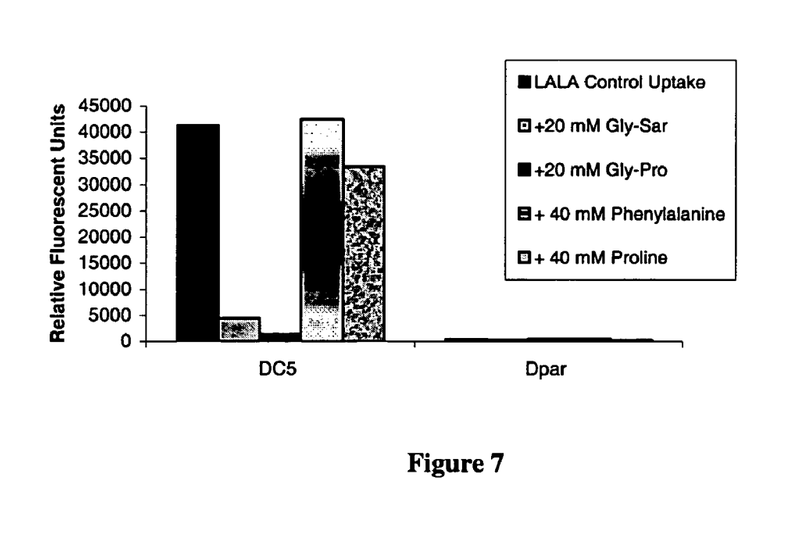
FIG. 7 is a bar graph showing specificity of LALA uptake. 25 μM of LALA is incubated in the presence 20 mM Gly-Sar (□), 20 mM Gly-Pro (■) 40 mM phenylalanine (▤) and 40 mM proline (■) in either the DC5 or the $D_{par}$ cell line. After 30 minutes the cells are washed and the fluorescence measured in the cells. LALA uptake was strongly inhibited by dipeptides but not by amino acids. There is minimal LALA uptake in the parental line $D_{par}$.
Figure 8:
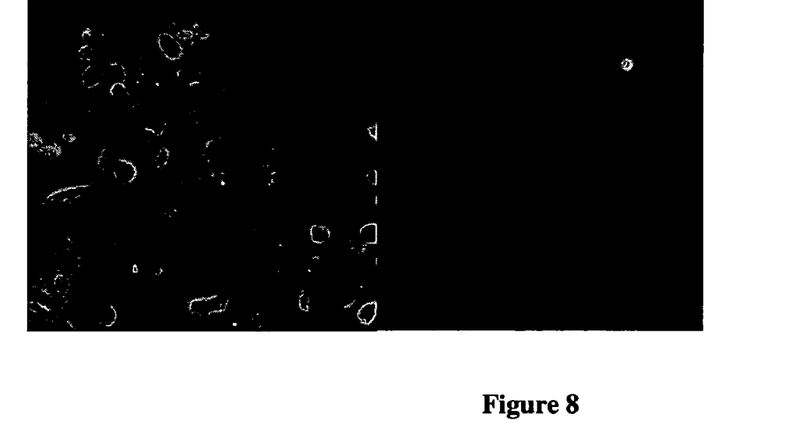
FIG. 8 is a fluorescent micrograph of LALA uptake into DC5 cells. Cells on a polylysine coated slide are incubated in the transport buffer with 50 μM LALA in the presence (right image) or absence (left image) the hPepT1 competitive inhibitor Gly-Pro (20 mM) for 20 minutes at room temperature. Cells are washed with cold PBS and viewed with an inverted microscope and imaged with a digital camera, with the images being at the same magnification and exposure time.

An inventive fluorescent marker compound of Example 2 (LALA) has the dipeptide L-Alanine-L-Lysine coupled through the ε-amino group of lysine to 7-amino-4-methyl-coumarin-3-acetic acid as follows:

As seen in FIGS. 5 and 6, the uptake of LALA is strongly inhibited by the dipeptide Gly-Pro, which serves as a competitive substrate for the hpept1 and is concentration dependent. CD5 and not D$_{par}$ specifically uptake LALA. DC5 and Dpar cells are incubated in transport buffer and the indicated concentrations of LALA added (♦) and (|), respectively. These experiments are repeated in the presence of 20 mM Gly-Pro for DC5 (◇) and Dpar (?). After 30 minutes, the cells are washed and processed for fluorescent determination. LALA is specifically taken up in the DC5 and not the parental cell line Dpar. This uptake is specifically inhibited by Gly-Pro. Thus, the combined system of DC5 and LALA will allow one to perform rapid initial screening of a large number of compounds for hpept1 interaction as was shown in the Example 1. FIG. 7 is a bar graph showing 25 μM of LALA is incubated in the presence 20 mM Gly-Sar (◉), 20 mM Gly-Pro (◼), 40 mM phenylalanine (◼), and 40 mM proline (☐) in either the DC5 or the D$_{par}$ cell line. After 30 minutes the cells are washed and the fluorescence measured in the cells. LALA uptake was strongly inhibited by dipeptides but not by amino acids. Because the marker probe is fluorescent, the system is amenable to more rapid throughput, through the use of automated fluorescent plate readers. Fluorescence imagining of LALA in DC5 cells is shown in FIG. 8, where cells on a polylysine coated slide are incubated in the transport buffer with 50 μM LALA in the presence (right image) or absence (left image) the hPepT1 competitive inhibitor Gly-Pro (20 mM) for 20 minutes at room temperature. Cells are washed with cold PBS and viewed with an inverted microscope and imaged with a digital camera, with the images being at the same magnification and exposure time.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

---

What is claimed is:

1. A compound for active agent delivery to cells of a subject of the formula:

(I)

where $C^a$ is methylene or an L-carbon atom; R is hydrogen or if $C^a$ is niethylene then R is methyl; $R^1$ is independently in each occurrence is a side chain of glycine, alanine, isoleucine, leucine, methionine, valine, phenylalanine, tyrosine, tryptophan, lysine, threonine, serine, histidine, glutamic acid, glutamine, cysteine, aspartic acid, asparagine, arginine, sarcosine, ornithine, citrulline, kynurenine, 5-hydroxytryptophan, 3-hydroxykynurenine, 3-aminotyrosine, or quisqualic acid; j is 1 or 2; $C^b$ is a D or L-carbon; $R^2$ and $R^3$ are independently in each occurrence a group consisting of a side chain and at least one of $R^2$ and $R^3$ has an active agent coupled through an active agent moiety to the side chain; said active agent is floxuridine, gemcitabine, cladribine, dacarbazine, melphalan, mercaptopurine, thioguanine, cis-platin, cytarabine; fludarabine, cidofovir, tenofovir, pentostatin, adenocard, adriamycin, allopurinol, alprostadil, amifostine, aminohippurate, argatroban, benztropine, bisphosphinate, bortezomib, busulfan, calcitriol, carboplatin, daunorubicin, dexamethasone, topotecan, docetaxel, dolasetron, doxorubicin, epirubicin, estradiol, famotidine, foscarnet, flumazenil, fosphenytoin, fulvestrant, hemin, ibutilide fumarate, irinotecan, levocarnitine, idamycin, sumatriptan, granisetron, metaraminol, metaraminol, methohexital, mitoxantrone, morphine, nalbuphine hydrochloride, nesacaine, oxaliplatin, palonosetron, pamidronate, pemetrexed, phytonadione, ranitidine, testosterone, tirofiban, toradol, triostat, valproate, vinorelbine tartrate, visudyne, zemplar, zemuron, zinecard, a coumarin, a cyanine, or a magnetic contrast agent; k is 0 or 1; l is 0 or 1 such that j+l equals 1 or 2; Q is oxygen when l is 0 and Q is NH when l is 1; $C^c$ is a racemic or L-carbon; $R^4$ is a side chain of glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine, hydroxylysine, citrulline, kynurenine, (4-aminophenyl)alanine, 3-(2'-naphthyl)alanine, 3-(1'-naphthyl) alanine, methionine sulfone, (t-butyl)alanine, (t-butyl)glycine, 4-hydroxyphenyl-glycine, aminoalanine, phenylglycine, vinylalanine, propargyl-glycine, 1,2,4-triazolo-3-alanine, thyronine, 6-hydroxytryptophan, 5-hydroxytryptophan, 3-hydroxykynurenine, 3-aminotyrosine, trifluoromethylalanine, 2-thienylalanine, (2-(4-pyridyl)ethyl)cysteine, 3,4-dimethoxy-phenylalanine, 3-(2'-thiazolyl)alanine, ibotenic acid, 1-amino-1-cyclopentane-carboxylic acid, 1-amino-1-cyclohexanecarboxylic acid, quisqualic acid, 3-(trifluoromethylphenyl)alanine, (cyclohexyl)glycine, thiohistidine, 3-methoxytyrosine, norleucine, norvaline, alloisoleucine, homoarginine, thioproline, dehydroproline, hydroxyproline, homoproline, indoline-2-carboxylic acid, 1,2,3,4-tetrahydroisoquinoline-3-carboxylic acid, 1,2,3,4-tetrahydroquinoline-2-carboxylic acid, α-amino-n-butyric acid, cyclohexylalanine, 2-amino-3-phenylbutyric acid, phenylalanine substituted at the ortho, meta, or para position of the phenyl moiety with one or two of the following groups: a ($C_1$ to $C_4$)alkyl, a ($C_1$ to $C_4$)alkoxy, a halogen or a nitro group, or substituted once with a methylenedioxy group; β-2- and 3-thienylalanine; β-2- and 3-furanylalanine; β-2-, 3- and 4-pyridylalanine; β-(benzothienyl-2- and 3-yl)alanine; β-(1- and 2-naphthyl)alanine; O-alkylated derivatives of serine, threonine or tyrosine; S-alkylated cysteine, S-alkylated homocysteine, the O-sulfate, O-phosphate and O-carboxylate esters of tyrosine; 3-(sulfo)tyrosine, 3-(carboxy)tyrosine, 3-(phospho)tyrosine, the 4-methane-sulfonic acid ester of tyrosine, 4-methanephosphonic acid ester of tyrosine, 3,5-diiodotyrosine, 3-nitrotyrosine, ε-alkyllysine, and delta-alkyl ornithine and a halogen substituent bonded via a phenyl where the halogen is fluorine, chlorine or bromine; and $R^5$ is hydrogen or $C_1$–$C_3$ alkyl.

2. The compound of claim 1 wherein $C^a$ is an L-carbon atom.

3. The compound of claim 2 wherein $R^1$ is the side chain selected from the group consisting of: glycine, alanine, isoleucine, leucine and valine.

4. The compound of claim 2 wherein $R^1$ is the side chain of alanine.

5. The compound of claim 1 wherein j is 1.

6. The compound of claim 5 where Q is oxygen and l is 0.

7. The compound of claim 6 where k is 0 and $R^2$ comprises the side chain of lysine coupled to the active agent through an amide bond.

8. The compound of claim 7 where $R^1$ is the side chain of alanine.

9. The compound of claim 1 wherein said active agent moiety coupled to said side chain is not an alcohol.

10. The compound of claim 1 wherein said active agent moiety coupled to said side chain is not an amine.

11. The compound of claim 1 wherein said active agent moiety is bonded to said side chain to form an amide bond.

12. The compound of claim 1 wherein said active agent moiety is bonded to said side chain to form an ester bond.

13. The compound of claim 1 wherein said active agent moiety is bonded to said side chain to form a phorsporamidate bond.

14. The compound of claim 1 wherein both $R^2$ and $R^3$ have the active agent and k is 1.

15. A compound for active agent delivery to cells of a subject of the formula:

(I)

where $C^a$ is methylene or an L-carbon atom; R is hydrogen or if $C^a$ is methylene then R is methyl; $R^1$ is independently in each occurrence is a side chain of glycinealanine, isoleucine, leucine, methionine, valine, phenylalanine, tyrosine, tryptophan, lysine, threonine, serine, histidine, glutamic acid, glutamine, cysteine, aspartic acid, asparagine, arginine; sarcosine, ornithine, citrulline, kynurenine, 5-hydroxytryptophan, 3-hydroxykynurenine, 3-aminotyrosine, or quisqualic acid; j is 1 or 2; $C^b$ is a D or L-carbon; $R^2$ and $R^3$ are independently in each occurrence a group consisting of an amino acid side chain and $R^2$ has an active agent coupled through an active agent moiety to the side chain; said active agent is floxuridine, gemcitabine, cladribine, dacarbazine, melphalan, mercaptopurine, thioguanine, cis-platin, cytarabine; fludarabine, cidofovir, tenofovir, pentostatin, adenocard, adriamycin, allopurinol, alprostadil, amifostine, aminohippurate, argatroban, benztropine, bisphosphinate, bortezomib, busulfan, calcitriol, carboplatin, daunorubicin, dexamethasone, topotecan, docetaxel, dolasetron, doxorubicin, epirubicin, estradiol, famotidine, foscarnet, flumazenil, fosphenytoin, fulvestrant, hemin, ibutilide fumarate, irinotecan, levocarnitine, idamycin, sumatriptan, granisetron, metaraminol, metaraminol, methohexital, mitoxantrone, morphine, nalbuphine hydrochloride, nesacaine, oxaliplatin, palonosetron, pamidronate, pemetrexed, phytonadione, ranitidine, testosterone, tirofiban, toradol, triostat, valproate, vinorelbine tartrate, visudyne, zemplar, zemuron, zinecard, a coumarin, a cyanine, or a magnetic contrast agent; k is 0 or 1, l is 0 or 1 such that j+l equals 1 or 2; Q is oxygen when l is 0 and Q is NH when l is 1; $C^c$ is a racemic or L-carbon; $R^4$ is a side chain of glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine, hydroxylysine, citrulline, kynurenine, (4-aminophenyl)alanine, 3-(2'-naphthyl)alanine, 3-(1'-naphthyl)alanine, methionine sulfone, (t-butyl)alanine, (t-butyl)glycine, 4-hydroxyphenyl-glycine, aminoalanine, phenylglycine, vinylalanine, propargyl-glycine, 1,2,4-triazolo-3-alanine, thyronine, 6-hydroxytryptophan, 5-hydroxytryptophan, 3-hydroxykynurenine, 3-aminotyrosine, trifluoromethylalanine, 2-thienylalanine,(2-(4-pyridyl)ethyl)cysteine, 3,4-dimethoxy-phenylalanine, 3-(2'-theazolyl)alanine, ibotenic acid, 1-amino-1-cyclopentanecarboxylic acid, 1-amino-1-cyclohexanecarboxylic acid, quisnualic acid, 3-(trifluoromethylphenyl)alanine, (cyclohexyl)glycine, thiohistidine, 3-methoxytyrosine, norleucine, norvaline, alloisoleucine, homoarginine, thioproline, dehydroproline, hydroxyproline, homoproline, indoline-2-carboxylic acid, 1,2,3,4-tetrahydroisoquinoline-3-carboxylic acid, 1,2,3,4-tetrahydroquinoline-2-carboxylic acid, α-amino-n-butyric acid, cyclohexylalanine, 2-amino-3-phenylbutyric acid, phenylalanine substituted at the ortho, meta, or para position of the phenyl moiety with one or two of the following groups: a $C_1$ ta $C_4$)alkyl, a ($C_1$ to $C_4$)alkoxy, a halogen or a nitro group, or substituted once with a methylenedioxy group; β-2- and 3-thienylalanine: β-2- and 3-furanylalanine: β-2-, 3- and 4-pyridylalanine; β-(benzothienyl-2- and 3-yl)alanine; β-(1- and 2-naphthyl)alanine; O-alkylated derivatives of serine, threonine or tyrosine; S-alkylated cysteine, S-alkylated homocysteine, the O-sulfate, O-phosphate and O-carboxylate esters of tyrosine; 3-(sulfo)tyrosine, 3-(carboxy)tyrosine, 3-(phospho)tyrosine, the 4-methane-sulfonic acid ester of tyrosine, 4-methanephosphonic acid ester of tyrosine, 3,5-diiodotyrosine, 3-nitrotyrosine, ε-alkyllysine, and delta-alkyl ornithine and a halogen substituent bonded via a phenyl where the halogen is fluorine, chlorine or bromine; and $R^5$ is hydrogen or $C_{1-3}$ alkyl;

wherein the side chain of $R^2$ further comprises a linker intermediate between said amino acid side chain and said active agent, said linker having a $C_0$–$C_{12}$ backbone.

16. The compound of claim 15 which is prepared by reacting one moiety of the linker with the amino acid side chain of $R^2$, and another moiety of the linker with said active agent.

* * * * *

SEQUENCE LISTING

<160> NUMBER OF SEQ ID NOS: 2

<210> SEQ ID NO 1
<211> LENGTH: 19
<212> TYPE: DNA
<213> ORGANISM: Artificial
<220> FEATURE:
<223> OTHER INFORMATION: oligonucleotide

<400> SEQUENCE: 1
gcagtcacct cagtaagct                                                19

<210> SEQ ID NO 2
<211> LENGTH: 18
<212> TYPE: DNA
<213> ORGANISM: Artificial
<220> FEATURE:
<223> OTHER INFORMATION: oligonucleotide

<400> SEQUENCE: 2
gctgctgatg tttgcata                                                 18